(12) United States Patent
Hood

(10) Patent No.: US 10,844,154 B2
(45) Date of Patent: Nov. 24, 2020

(54) PROLIFEROUS COPOLYMERS COMPRISING LACTAMIC MOIETIES

(71) Applicant: ISP INVESTMENTS LLC, Wilmington, DE (US)

(72) Inventor: David K. Hood, Basking Ridge, NJ (US)

(73) Assignee: ISP INVESTMENTS LLC, Wilmington, DE (US)

( * ) Notice: Subject to any disclaimer, the term of this patent is extended or adjusted under 35 U.S.C. 154(b) by 92 days.

(21) Appl. No.: 15/777,691

(22) PCT Filed: Nov. 21, 2016

(86) PCT No.: PCT/US2016/063052
§ 371 (c)(1),
(2) Date: May 21, 2018

(87) PCT Pub. No.: WO2017/087941
PCT Pub. Date: May 26, 2017

(65) Prior Publication Data
US 2018/0340034 A1    Nov. 29, 2018

Related U.S. Application Data

(60) Provisional application No. 62/258,059, filed on Nov. 20, 2015.

(51) Int. Cl.
| | | |
|---|---|---|
| C08F 226/06 | (2006.01) |
| C09D 4/00 | (2006.01) |
| C11D 3/37 | (2006.01) |
| C08F 220/36 | (2006.01) |
| C08F 226/10 | (2006.01) |
| C12H 1/056 | (2006.01) |
| C11D 3/32 | (2006.01) |
| C08F 220/18 | (2006.01) |
| C08K 5/00 | (2006.01) |
| C08L 77/02 | (2006.01) |
| A61K 9/20 | (2006.01) |
| C08F 220/60 | (2006.01) |

(52) U.S. Cl.
CPC .......... *C08F 226/06* (2013.01); *C08F 220/18* (2013.01); *C08F 220/36* (2013.01); *C08F 226/10* (2013.01); *C08K 5/0025* (2013.01); *C08L 77/02* (2013.01); *C09D 4/00* (2013.01); *C11D 3/323* (2013.01); *C11D 3/3776* (2013.01); *C12H 1/0424* (2013.01); *A61K 9/2027* (2013.01); *C08F 220/603* (2020.02); *C08L 2312/00* (2013.01)

(58) Field of Classification Search
CPC ................................ C08F 226/06; C08L 77/02
See application file for complete search history.

(56) References Cited

U.S. PATENT DOCUMENTS

| | | | |
|---|---|---|---|
| 5,856,364 A | 1/1999 | Martin et al. | |
| 6,268,511 B1* | 7/2001 | Li | C07D 207/27 523/108 |
| 6,465,588 B1* | 10/2002 | Li | C08F 220/52 526/258 |
| 9,169,344 B2* | 10/2015 | Hood | C08F 8/00 |
| 9,464,151 B2* | 10/2016 | Hood | C09D 139/06 |
| 9,757,704 B2* | 9/2017 | Hood | B01J 13/14 |
| 2004/0054066 A1 | 3/2004 | Malawer et al. | |
| 2010/0069535 A1 | 3/2010 | Suzuki et al. | |
| 2011/0293540 A1* | 12/2011 | Musa | C08F 226/08 424/49 |
| 2012/0276211 A1* | 11/2012 | Hood | C08F 226/06 424/501 |
| 2013/0261268 A1* | 10/2013 | Hood | C08F 226/06 525/326.9 |
| 2014/0296441 A1* | 10/2014 | Hood | C08F 226/10 525/303 |
| 2018/0327628 A1* | 11/2018 | Musa | C09J 139/04 |
| 2018/0333345 A1* | 11/2018 | Tallon | A61K 8/8152 |
| 2018/0346804 A1* | 12/2018 | Blazewicz | A61K 31/79 |
| 2018/0369120 A1* | 12/2018 | Gamez-Garcia | A61Q 5/12 |

FOREIGN PATENT DOCUMENTS

JP    5-80279 A  *  4/1993  ............ C08F 220/18

OTHER PUBLICATIONS

JP 5-80279 A (Apr. 2, 1993); machine translation (Year: 1993).*
International Search Report, PCT/US2016/063052 published on May 26, 2017.

* cited by examiner

*Primary Examiner* — Rip A Lee
(74) *Attorney, Agent, or Firm* — William J. Davis; Nathalie Tietcheu

(57) ABSTRACT

This invention relates to the preparation and utility of proliferous polymer compositions comprising repeating units derived from (a) a monomer comprising at least one functionalized or unfunctionalized acryloyl moiety and at least one lactam moiety, (b) an optional monomer comprising at least one double bond, and (c) a at least one cross-linker.

6 Claims, No Drawings

PROLIFEROUS COPOLYMERS COMPRISING LACTAMIC MOIETIES

CROSS-REFERENCE TO RELATED APPLICATIONS

This application is the national stage entry of International Patent Application No. PCT/US2015/063052 filed on Nov. 21, 2016, which claims priority to Provisional Patent Application No. 62/258,059 filed on Nov. 20, 2015, which are incorporated herein by reference in their entireties.

BACKGROUND OF THE INVENTION

Field of Invention

This application provides proliferous polymer compositions comprising repeating units derived from (a) a monomer comprising at least one functionalized or unfunctionalized acryloyl moiety and at least one lactam moiety (monomer A), (b) an optional monomer comprising at least one double bond (monomer $B_{Xn}$), and (c) at least one cross-linker (monomer $C_{Xn}$). The application further provides formulations and applications of the aforementioned polymer compositions in various industrial arts including coatings, pharmaceutical, nutrition and personal care.

Description of Prior Art

U.S. Pat. No. 3,759,880 discloses the manufacture of an insoluble, slightly swellable poly-N-vinylpyrrolidone in the presence of unsaturated cyclic amides and an oxidizable metal. Example 1 employs N,N'-divinylimidazolidone-2 or 1,3-divinyl imidazolidin-2-one (DVI). The chemical structures for N-vinyl-2-pyrrolidone and DVI are presented in the FIG. 1 below.

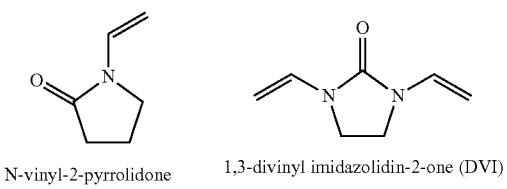

N-vinyl-2-pyrrolidone    1,3-divinyl imidazolidin-2-one (DVI)

Figure 1

U.S. Pat. No. 3,992,562 A discloses the manufacture of insoluble polyvinyl lactams by polymerization in the absence of oxygen and in the presence of sulfur compounds having a functionality of less than 6.

U.S. Pat. No. 5,663,258 discloses a strongly swellable, moderately cross-linked copolymer of vinyl pyrrolidone and vinyl acetate made by precipitation polymerization in the presence of a free radical initiator. The copolymer obtained by this process had unique gel volume and viscosity properties which enabled it to thicken aqueous and non-aqueous solutions effectively.

U.S. Pat. No. 6,806,334 B2 discloses an excipient for a pharmaceutical tablet which is a proliferous copolymer of vinyl pyrrolidone and vinyl acetate, to provide the tablet with rapid dissolution and disintegration properties, and, also reduced hygroscopicity.

EP 0979649A2 discloses copolymers of vinyl pyrrolidone and vinyl acetate made by free radical polymerization, optionally with an added crosslinking agent, which process provided copolymers having K-value of 50 to 200. Such copolymers were considered suitable for use as a matrix material in pharmaceutical or cosmetic preparations.

U.S. Pat. No. 5,393,854 discloses the preparation of the isomeric compound 1-vinyl-3(E)-ethylidene pyrrolidone (EVP). The chemical structure of EVP is presented in FIG. 2 below.

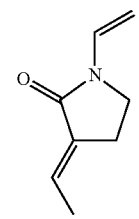

1-vinyl-3(E)-ethylidene pyrrolidone (EVP)

Figure 2 which, in solid form, had a purity of at least 95% and were white, needle-shaped crystals having a melting point of 59-61° C. This isomeric compound was used as a crosslinking agent in the proliferous polymerization of vinyl pyrrolidone. However, none of these references disclose or suggest the preparation and utility of proliferous copolymers derived from at least one functionalized or unfunctionalized acryloyl moiety and at least one lactam moiety and at least one cross-linker.

U.S. Pat. No. 5,393,854 also discloses a polymerizable composition of vinyl pyrrolidone and isomeric EVP for proliferous polymerization of vinyl pyrrolidone.

WO/2013/082359 A1 discloses monomeric vinyl compositions suitable for use as cross-linkers in proliferous polymerizations processes.

U.S. Pat. No. 8,623,978 B2 discloses a process for the preparation of low-peroxide cross-linked vinyl lactam polymer by free-radical polymerization in the presence of at least one organic substance acting as antioxidant, low-peroxide cross-linked vinyl lactam polymer obtainable by this process, and its use. However, none of these references, disclosed or suggest the preparation and utility of proliferous copolymers derived from at least one monomer comprising at least one functionalized or unfunctionalized acryloyl moiety and at least one lactam moiety and at least one cross-linker.

A polymer produced by a proliferous or popcorn polymerization process is described, as presented in the Alger, M. S. M., in *Polymer Science Dictionary*, Chapman and Hall, London, U K, 1997, p. 467, as the separation during a free radical polymerization of small, opaque polymer nodules (or popcorn) which, once formed, proliferate rapidly to yield a cross-linked insoluble product of larger volume than the original monomer. Once the cross-link has formed, local termination is very low due to the low mobility of the radicals in the popcorn, so that the polymerization rate is high.

Accordingly, it is an object of the present application to provide for the preparation and utility of proliferous polymer compositions comprising repeating units derived from at least one monomer comprising at least one functionalized or unfunctionalized acryloyl moiety and at least one lactam moiety and at least one cross-linker.

SUMMARY OF THE INVENTION

In a first aspect, the present application provides a proliferous polymer composition comprising repeating units derived from (a) a monomer comprising at least one functionalized or unfunctionalized acryloyl moiety and at least one lactam moiety and (b) at least one cross-linker.

In a second aspect, there is provided a proliferous polymer composition comprising repeating units derived from (a) a monomer comprising at least one functionalized or unfunctionalized acryloyl moiety and at least one lactam moiety, (b) at least one monomer comprising at least one double bond, and (c) at least one cross-linker.

In a third aspect, there is provided formulations comprising the above described proliferous polymer compositions. Non-limiting examples of such formulations include malodor absorbents, adhesives, aerosols, agricultural agents, anti-soil redeposition agents, battery compositions, beverages, biocides, cementing agents, cleaning agents, coatings, conductive materials, personal care compositions, oral care compositions, hair care compositions, skin care compositions, pigments, detergents, disintegrants, dispersants, pharmaceuticals, electronic compositions, encapsulation compositions, food compositions, household industrial and institutional compositions, inks, compositions comprising iodine, compositions comprising silicate, compositions comprising peroxide, compositions comprising carbon materials, interlaminate adhesives, lithographic solutions, membranes, metal working fluids, oilfield compositions, paints, paper compositions, plasters, plastics, printing compositions, proppants, refractive index modifiers, sequestrants, self-healing coatings, shale swell inhibitors, soil release agents, static control agents, and wood-care agents.

DETAILED DESCRIPTION

It is to be understood that the present application is not limited to the details of construction and the arrangement of the components or steps or methodologies set forth in the following description or illustrated in the drawings. The disclosed and/or claimed inventive concept(s) is capable of other aspects or of being practiced or carried out in various ways. Also, it is to be understood that the phraseology and terminology employed herein is for the purpose of description and should not be regarded as limiting.

Unless otherwise defined herein, technical terms used in connection with the disclosed and/or claimed inventive concept(s) shall have the meanings that are commonly understood by those of ordinary skill in the art. Further, unless otherwise required by context, singular terms shall include pluralities and plural terms shall include the singular.

All patents, published patent applications, and non-patent publications referenced in any portion of this application are herein expressly incorporated by reference herein their entirety to the same extent as if each individual patent or publication was specifically and individually indicated to be incorporated by reference.

All of the articles and/or methods disclosed herein can be made and executed without undue experimentation in light of the present disclosure. While the articles and methods of the disclosed and/or claimed inventive concept(s) have been described in terms of aspects, it will be apparent to those of ordinary skill in the art that variations may be applied to the articles and/or methods and in the steps or in the sequence of steps of the method described herein without departing from the concept, spirit and scope of the disclosed and/or claimed inventive concept(s). All such similar substitutes and modifications apparent to those skilled in the art are deemed to be within the spirit, scope and concept of the disclosed and/or claimed inventive concept(s).

As utilized in accordance with the disclosure, the following terms, unless otherwise indicated, shall be understood to have the following meanings.

The use of the word "a" or "an" when used in conjunction with the term "comprising" may mean "one," but it is also consistent with the meaning of "one or more," "at least one," and "one or more than one." The use of the term "or" is used to mean "and/or" unless explicitly indicated to refer to alternatives only if the alternatives are mutually exclusive, although the disclosure supports a definition that refers to only alternatives and "and/or."

Throughout this application, the term "about" is used to indicate that a value includes the inherent variation of error for the quantifying device, the method being employed to determine the value, or the variation that exists among the study subjects. For example, but not by way of limitation, when the term "about" is utilized, the designated value may vary by plus or minus twelve percent, or eleven percent, or ten percent, or nine percent, or eight percent, or seven percent, or six percent, or five percent, or four percent, or three percent, or two percent, or one percent.

The use of the term "at least one" will be understood to include one as well as any quantity more than one, including but not limited to, 1, 2, 3, 4, 5, 10, 15, 20, 30, 40, 50, 100, etc. The term "at least one" may extend up to 100 or 1000 or more depending on the term to which it is attached. In addition, the quantities of 100/1000 are not to be considered limiting as lower or higher limits may also produce satisfactory results. In addition, the use of the term "at least one of X, Y, and Z" will be understood to include X alone, Y alone, and Z alone, as well as any combination of X, Y, and Z. The use of ordinal number terminology (i.e., "first", "second", "third", "fourth", etc.) is solely for the purpose of differentiating between two or more items and, unless otherwise stated, is not meant to imply any sequence or order or importance to one item over another or any order of addition.

As used herein, the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps. The term "or combinations thereof" as used herein refers to all permutations and combinations of the listed items preceding the term. For example, "A, $B_{Xn}$, $B_{Xn+1}$, or combinations thereof" is intended to include at least one of: A, $B_{Xn}$, $B_{Xn+1}$, $AB_{Xn}$, $A B_{Xn+1}$, $B_{Xn}B_{Xn+1}$, or $AB_{Xn}B_{Xn+1}$ and, if order is important in a particular context, also $B_{Xn}A$, $B_{Xn+1}A$, $B_{Xn+1}B_{Xn}$, $B_{Xn+1}B_{Xn}A$, $B_{Xn}B_{Xn+1}A$, $AB_{Xn+1}B_{Xn}$, $B_{Xn}AB_{Xn+1}$, or $B_{Xn+1}AB_{Xn}$. Continuing with this example, expressly included are combinations that contain repeats of one or more item or term, such as $B_{Xn}B_{Xn}$, AAA, $MB_{Xn}$, $B_{Xn}B_{Xn}B_{Xn+1}$, $AAAB_{Xn}B_{Xn+1}B_{Xn+1}B_{Xn+1}B_{Xn+1}$, $B_{Xn+1}B_{Xn+1}B_{Xn}B_{Xn}AAA$, $B_{Xn+1}A B_{Xn}AB_{Xn}B_{Xn}$, and so forth. The skilled artisan will understand that typically there is no limit on the number of items or terms in any combination, unless otherwise apparent from the context.

The term "each independently selected from the group consisting of" means when a group appears more than once in a structure, that group may be selected independently each time it appears.

The term "hydrocarbyl" includes straight-chain and branched-chain alkyl, alkenyl, alkynyl, cycloalkyl, cycloalkenyl, aryl groups, and combinations thereof with optional heteroatom(s). A hydrocarbyl group may be mono-, di- or polyvalent.

The term "alkyl" refers to a functionalized or unfunctionalized, monovalent, straight-chain, branched-chain, or cyclic $C_1$-$C_{60}$ hydrocarbyl group optionally having one or more heteroatoms. In one non-limiting embodiment, an alkyl is a $C_1$-$C_{45}$ hydrocarbyl group. In another non-limiting embodiment, an alkyl is a $C_1$-$C_{30}$ hydrocarbyl group. Non-limiting examples of alkyl include methyl, ethyl, n-propyl, isopropyl, n-butyl, isobutyl, tert-butyl, n-pentyl, isopentyl, n-hexyl, n-heptyl, n-octyl, 2-ethylhexyl, tert-octyl, iso-norbornyl, n-dodecyl, tert-dodecyl, n-tetradecyl, n-hexadecyl, n-octadecyl, n-eicosyl, cyclobutyl, cyclopentyl, cyclohexyl, and the like. The definition of "alkyl" also includes groups obtained by combinations of straight-chain, branched-chain and/or cyclic structures.

The term "aryl" refers to a functionalized or unfunctionalized, monovalent, aromatic hydrocarbyl group optionally having one or more heteroatoms. The definition of aryl includes carbocyclic and heterocyclic aromatic groups. Non-limiting examples of aryl groups include phenyl, naphthyl, indenyl, indanyl, azulenyl, fluorenyl, anthracenyl, furyl, thienyl, pyridyl, pyrrolyl, oxazolyl, thiazolyl, imidazolyl, pyrazolyl, 2-pyrazolinyl, pyrazolidinyl, isoxazolyl, isothiazolyl, 1,2,3-oxadiazolyl, 1,2,3-triazolyl, 1,3,4-thiadiazolyl, pyridazinyl, pyrimidinyl, pyrazinyl, 1,3,5-triazinyl, 1,3,5-trithianyl, indolizinyl, indolyl, isoindolyl, 3H-indolyl, indolinyl, benzo[b]furanyl, 2,3-dihydrobenzofuranyl, benzo[b]thiophenyl, 1H-indazolyl, benzimidazolyl, benzthiazolyl, purinyl, 4H-quinolizinyl, isoquinolinyl, cinnolinyl, phthalazinyl, quinazolinyl, quinoxalinyl, 1,8-naphthridinyl, pteridinyl, carbazolyl, acridinyl, phenazinyl, phenothiazinyl, phenoxyazinyl, pyrazolo[1,5-c]triazinyl, and the like.

The term "aralkyl" refers to an alkyl group comprising one or more aryl substituent(s) wherein "aryl" and "alkyl" are as defined above. Non-limiting examples of aralkyl groups include benzyl, 2-phenyl-ethyl, 3-phenyl-propyl, 4-phenyl-butyl, 5-phenyl-pentyl, 4-phenylcyclohexyl, 4-benzylcyclohexyl, 4-phenylcyclohexylmethyl, 4-benzylcyclohexylmethyl, and the like.

The term "alkylene" refers to a functionalized or unfunctionalized, divalent, straight-chain, branched-chain, or cyclic $C_1$-$C_{40}$ hydrocarbyl group optionally having one or more heteroatoms. In one non-limiting embodiment, an alkylene is a $C_1$-$C_{30}$ group. In another non-limiting embodiment, an alkylene is a $C_1$-$C_{20}$ group. Non-limiting examples of alkylene groups include:

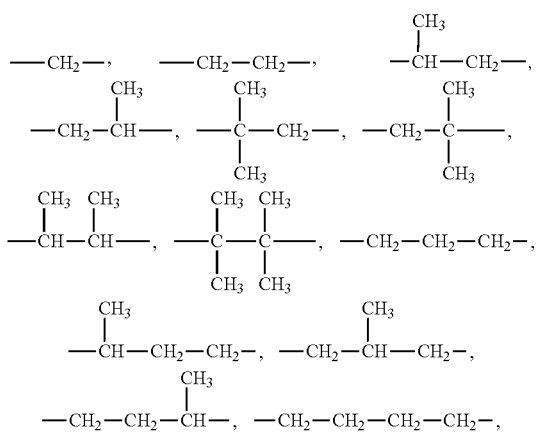

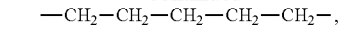
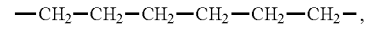
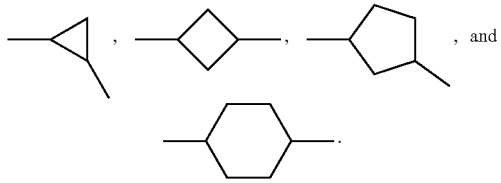

The term "arylene" refers to a functionalized or unfunctionalized, divalent, aromatic hydrocarbyl group optionally having one or more heteroatoms. The definition of arylene includes carbocyclic and heterocyclic groups. Non-limiting examples of arylene groups include phenylene, naphthylene, pyridinylene, and the like.

The term "heteroatom" refers to oxygen, nitrogen, sulfur, silicon, phosphorous, or halogen. The heteroatom(s) may be present as a part of one or more heteroatom-containing functional groups. Non-limiting examples of heteroatom-containing functional groups include ether, hydroxy, epoxy, carbonyl, carboxamide, carboxylic ester, carboxylic acid, imine, imide, amine, sulfonic, sulfonamide, phosphonic, and silane groups. The heteroatom(s) may also be present as a part of a ring such as in heteroaryl and heteroarylene groups.

The term "halogen" or "halo" refers to Cl, Br, I, or F.

The term "ammonium" includes protonated $NH_3$ and protonated primary, secondary, and tertiary organic amines.

The term "functionalized" with reference to any moiety refers to the presence of one or more functional groups in the moiety. Various functional groups may be introduced in a moiety by way of one or more functionalization reactions known to a person having ordinary skill in the art. Non-limiting examples of functionalization reactions include: alkylation, epoxidation, sulfonation, hydrolysis, amidation, esterification, hydroxylation, dihydroxylation, amination, ammonolysis, acylation, nitration, oxidation, dehydration, elimination, hydration, dehydrogenation, hydrogenation, acetalization, halogenation, dehydrohalogenation, Michael addition, aldol condensation, Canizzaro reaction, Mannich reaction, Clasien condensation, Suzuki coupling, and the like. In one non-limiting embodiment, the term "functionalized" with reference to any moiety refers to the presence of one more functional groups selected from the group consisting of alkyl, alkenyl, hydroxyl, carboxyl, halogen, alkoxy, amino, imino, and combinations thereof, in the moiety.

The term "monomer" refers to a small molecule that chemically bonds during polymerization to one or more monomers of the same or different kind to form a polymer.

The term "polymer" refers to a large molecule comprising one or more types of monomer residues (repeating units) connected by covalent chemical bonds. By this definition, polymer encompasses compounds wherein the number of monomer units may range from very few, which more commonly may be called as oligomers, to very many. Non-limiting examples of polymers include homopolymers, and non-homopolymers such as copolymers, terpolymers, tetrapolymers and the higher analogues. The polymer may have a random, block, and/or alternating architecture.

The term "homopolymer" refers to a polymer that consists essentially of a single monomer type.

The term "non-homopolymer" refers to a polymer that comprises more than one monomer types.

The term "copolymer" refers to a non-homopolymer that comprises two different monomer types.

The term "terpolymer" refers to a non-homopolymer that comprises three different monomer types. The term "branched" refers to any non-linear molecular structure. The term includes both branched and hyper-branched structures.

The term "non-ionic polymer" refers to a polymer that does not exhibit a charge. For example, poly(vinyl alcohol).

The term "cationic polymer" refers to a polymer that exhibits a positive charge. For example, quaternary polymers of vinyl pyrrolidone and vinyl imidazole.

The term "anionic polymer" refers to a polymer that exhibits a negative charge. For example, poly(acrylic acid-co-maleic acid).

The term "zwitterionic polymer" refers to a polymer that exhibits both positive and negative charges. For example, poly(vinyl sulphobetaine) as in Wielema, T. A.; Engberts, J. B. F. N., *Eur. Polym. J.*, Vol. 23, No. 12, pp. 947-950, 1987 (this reference is incorporated in its entirety by reference).

The terms "personal care composition" and "cosmetics" refer to compositions intended for use on or in the human body, such as skin, sun, hair, oral, cosmetic, and preservative compositions, including those to alter the color and appearance of the skin and hair.

The phrase "pharmaceutically acceptable" or "cosmetically acceptable" refers to molecular entities and compositions that are generally regarded as safe. Particularly, as used herein, the term "pharmaceutically acceptable" or "cosmetically acceptable" means approved by a regulatory agency of the appropriate governmental agency or listed in the U.S. Pharmacopoeia or other generally recognized pharmacopoeia for use in animals, and more particularly in humans.

The term "pharmaceutical composition" refers to any composition comprising at least one pharmaceutically active ingredient, as well as any product which results, directly or indirectly, from combination, complexation, or aggregation of any two or more of the ingredients, from dissociation of one or more of the ingredients, or from other types of reactions or interactions of one or more of the ingredients.

The term "pharmaceutically active ingredient" should be construed in a broad sense as including any ingredient considered to have a therapeutic effect when delivered to a subject in need thereof and further being regulated by drug authorities like CDER, EMEA, TAG etc. Pharmaceutically active ingredients may act systemically upon oral consumption, or locally such as when present in the buccal cavity, on the skin, etc. They may also be delivered across the skin as in transdermal drug delivery systems.

The term "coating composition" refers to an aqueous-based or solvent-based liquid composition that may be applied to a substrate and thereafter solidified (for example, by radiation, air curing, post-crosslinking or ambient temperature drying) to form a hardened coating on the substrate.

The term "powder" refers to any dry substance in the form of fine, dust-like particles. Compositions in this form can be dusting.

The term "granule" refers to a small grain or particle, which is generally larger in size than a powder that exhibits a decreased tendency to exhibit dusting. Compositions in this form tend to be less dusting.

The term "prill" refers to small round or acicular aggregates of material that are artificially prepared, often from a blend of materials. Compositions in this form tend to be less dusting.

The term "oilfield composition" refers to a composition that may be used in the exploration, extraction, recovery, and/or completion of any hydrocarbon. Non-limiting examples of oilfield compositions include drilling fluids, cementing fluids, anti-agglomerants, kinetic hydrate inhibitors, shale swelling inhibitors, drilling muds, servicing fluids, proppants, gravel packing muds, friction reducers, fracturing fluids, completion fluids, and work over fluids.

The term "acryloyl" refers to a moiety having the generic structure:

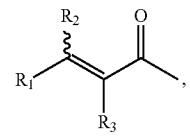

wherein each $R_1$, $R_2$, and $R_3$ is independently selected from the group consisting of hydrogen and functionalized and unfunctionalized alkyl, alkenyl, aryl, nitrile, formyl, carboxyl, carboxylate salt, carboxylic ester, carboxamide, halogen, thiocarboxylate, and combinations thereof.

All percentages, ratio, and proportions used herein are based on a weight basis unless otherwise specified.

In a first aspect, the present application provides a proliferous polymer composition comprising repeating units derived from (a) a monomer comprising at least one functionalized or unfunctionalized acryloyl moiety and at least one lactam moiety (monomer A) and (b) at least one cross-linker (monomer $C_{Xn}$).

In one non-limiting embodiment, the monomer comprising at least one functionalized or unfunctionalized acryloyl moiety and at least one lactam moiety (monomer A) has the structure:

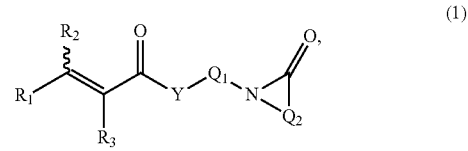

(1)

wherein each $R_1$ $R_2$ and $R_3$ is independently selected from the group consisting of hydrogen, halogens, functionalized and unfunctionalized $C_1$-$C_4$ alkyl, and

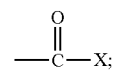

each X is independently selected from the group consisting of $OR_4$, OM, halogen, $N(R_5)(R_6)$,

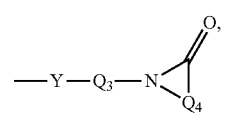

and combinations thereof; each Y is independently oxygen, $NR_7$ or sulfur; each $R_4$, $R_5$, $R_6$ and $R_7$ is independently selected from the group consisting of hydrogen and functionalized and unfunctionalized alkyl; each M is independently selected from the group consisting of metal ions, ammonium ions, organic ammonium cations, and combinations thereof; and each $Q_1$, $Q_2$, $Q_3$, and $Q_4$ is independently selected from the group consisting of functionalized and unfunctionalized alkylene.

In one non-limiting embodiment, each $Q_1$, $Q_2$, $Q_3$, and $Q_4$ is independently selected from the group consisting of functionalized and unfunctionalized $C_1$-$C_{12}$ alkylene. Non-limiting examples of alkylene groups include —$CH_2$—, —$CH_2$—$CH_2$—, —$CH(CH_3)$—$CH_2$—, —$CH_2$—$CH(CH_3)$—, —$C(CH_3)_2$—$CH_2$—, —$CH_2$—$C(CH_3)_2$—, —$CH(CH_3)$—$CH(CH_3)$—, —$C(CH_3)_2$—$C(CH_3)_2$—, —$CH_2$—$CH_2$—$CH_2$—, —$CH(CH_3)$—$CH_2$—$CH_2$—, —$CH_2$—$CH(CH_3)$—$CH_2$—, —$CH_2$—$CH_2$—$CH(CH_3)$—, —$CH_2$—$CH_2$—$CH_2$—$CH_2$—, —$CH_2$—$CH_2$—$CH_2$—$CH_2$—$CH_2$—, and —$CH_2$—$CH_2$—$CH_2$—$CH_2$—$CH_2$—$CH_2$—.

In one non-limiting embodiment, each $R_1$, $R_2$ and $R_3$ is independently selected from the group consisting of hydrogen, methyl and combinations thereof. Particularly, $R_1$ and $R_2$ are hydrogens and $R_3$ is hydrogen or methyl.

In another non-limiting embodiment, each $R_1$ and $R_3$ is independently hydrogen or methyl; $R_2$ is

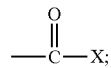

X is selected from the group consisting of $OR_4$, OM, halogens, and $N(R_5)(R_6)$; each $R_4$, $R_5$, and $R_6$ is independently selected from the group consisting of hydrogen and functionalized and unfunctionalized alkyl; and each M is independently selected from the group consisting of metal ions, ammonium ions, organic ammonium cations, and combinations thereof. Particularly, $R_1$ and $R_3$ are hydrogens and $R_2$ is

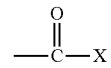

X is selected from the group consisting of $OR_4$, OM and $N(R_5)(R_6)$; each $R_4$, $R_5$, and $R_6$ is independently selected from the group consisting of hydrogen and functionalized and unfunctionalized $C_1$-$C_4$ alkyl; and each M is independently selected from the group consisting of metal ions, ammonium ions, organic ammonium cations, and combinations thereof.

The monomer defined by structure (1), maybe be synthesized using methods recorded in the art, e.g., by reaction of an N-hydroxylalkyl lactam with an acrylate, (meth)acrylate, anhydride, or similar compounds. Production methods include those described in U.S. Pat. Nos. 2,882,262; 5,523,340; 6,369,163; U.S. Patent Application Publication 2007/123673; GB 924,623; 930,668; and 1,404,989; WO 03/006569; and EP 385918. Each of the previous disclosures are hereby incorporated herein by reference in its entirety.

In one non-limiting embodiment, the monomer having at least one functionalized or unfunctionalized acryloyl moiety and at least one lactam moiety (monomer A) has a structure selected from the group consisting of:

(2)
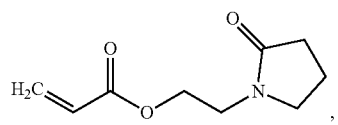

(3)
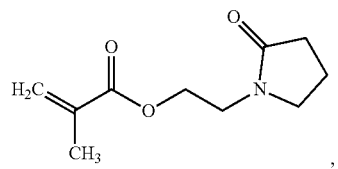

(4)
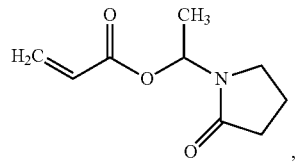

(5)
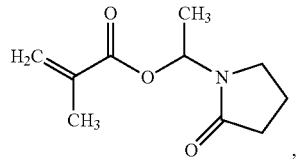

(6)
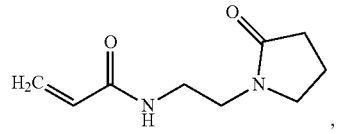

(7)
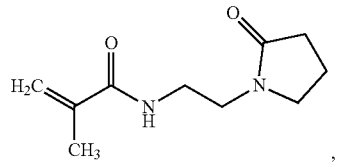

(8)
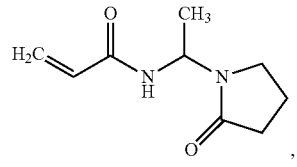

(9)
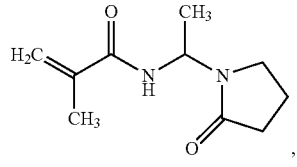

(10)
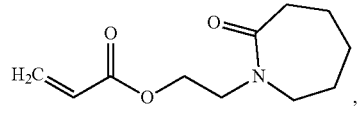

(11)
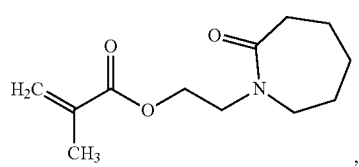

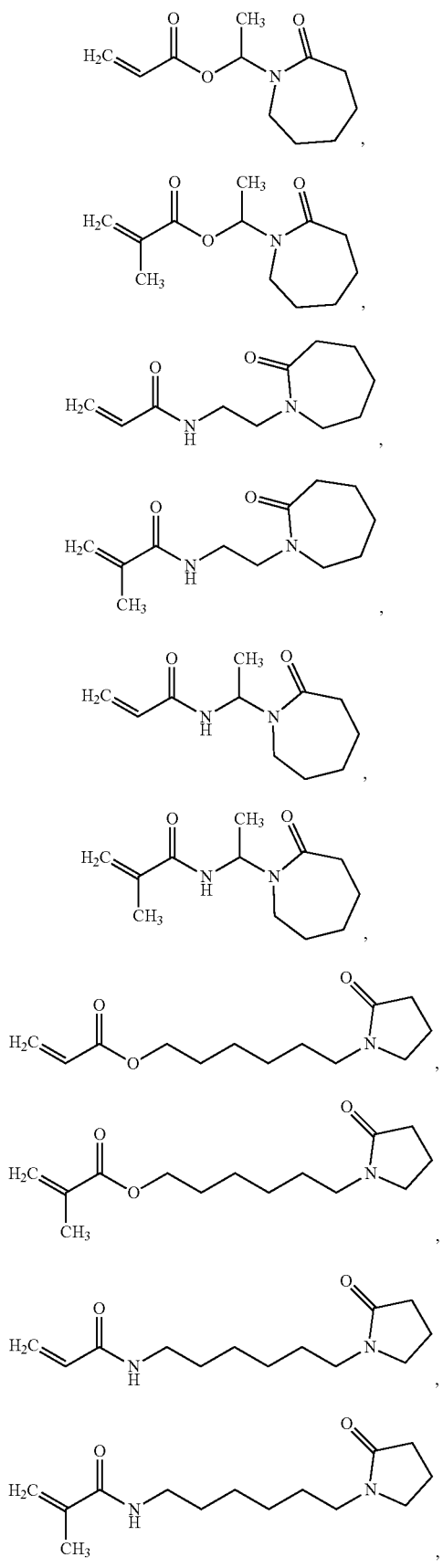

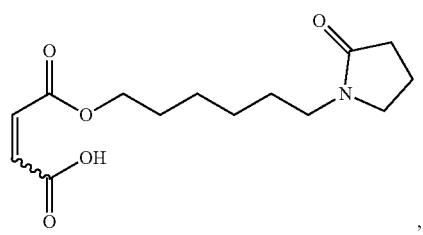
(30)
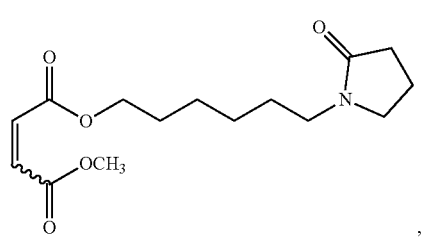
(31)
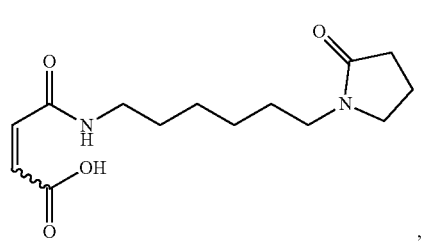
(32)
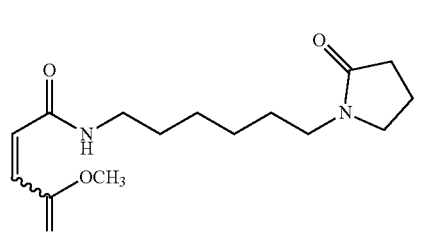
(33)
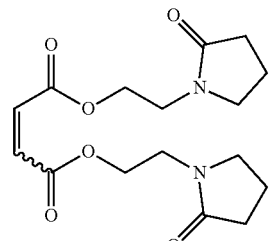
(34)
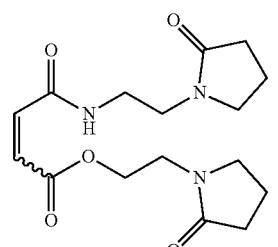
(35)
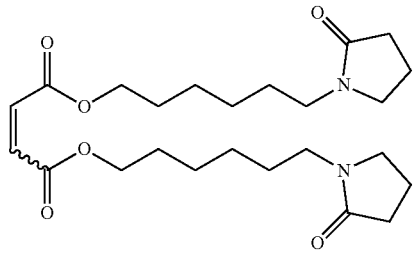
(36)
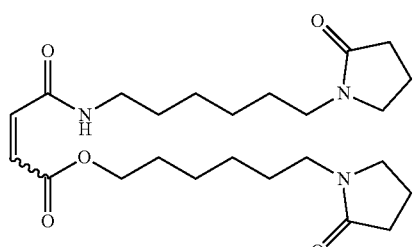
(37)
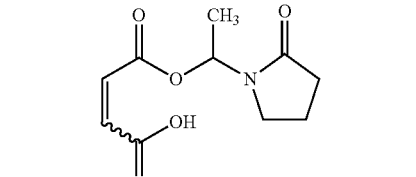
(38)
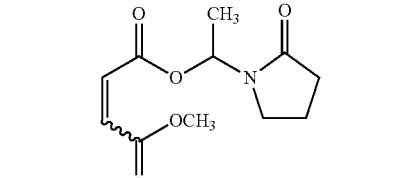
(39)
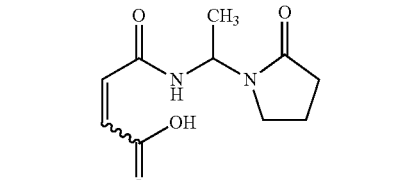
(40)
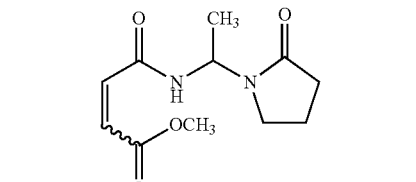
(41)
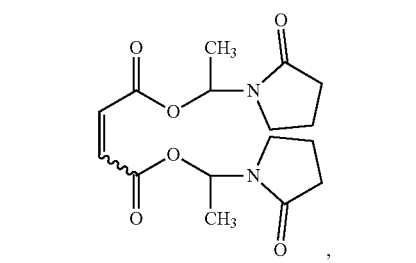
(42)

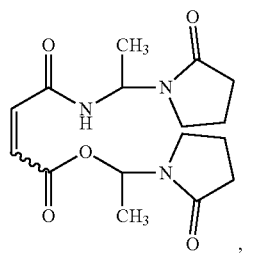
(43)
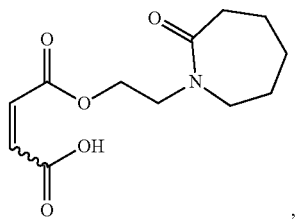
(44)
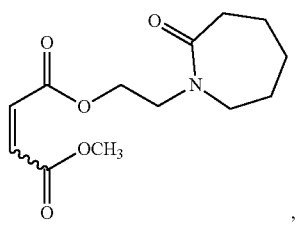
(45)
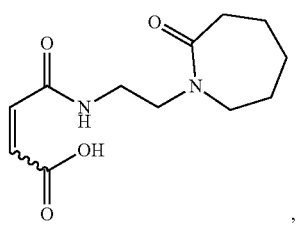
(46)
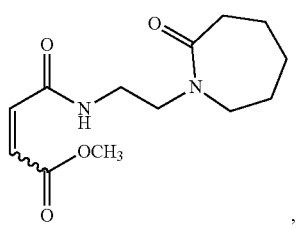
(47)
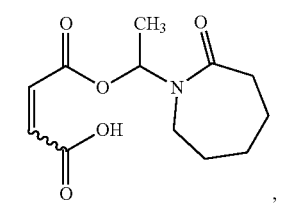
(48)
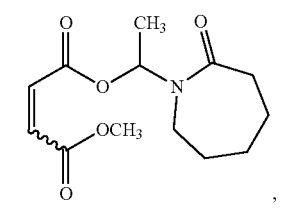
(49)
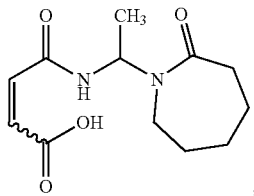
(50)
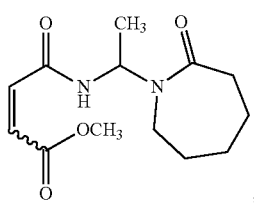
(51)
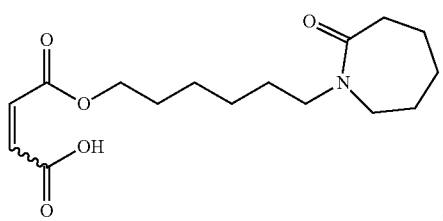
(52)
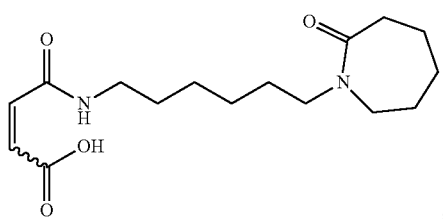
(53)
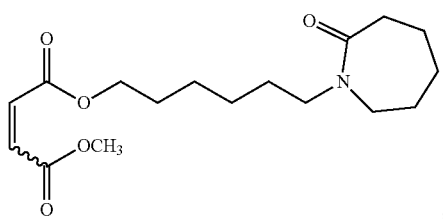
(54)
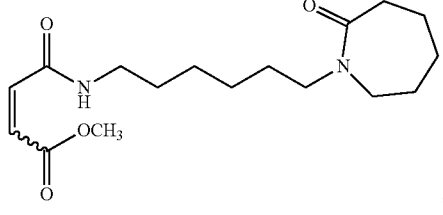
(55)
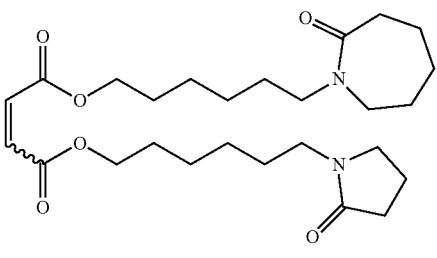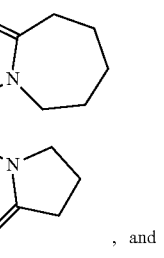
(56)
, and

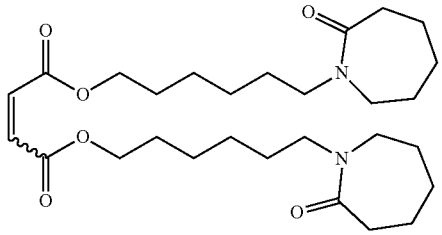

(57)

The lactam-containing monomers shown in structures (2) through (57) can be obtained from condensation reactions that include an N-hydroxyalkyl lactam and an unsaturated carboxylic acid, an acrylate, a (meth)acrylate, or an anhydride. Suitable N-hydroxyalkyl lactams include N-hydroxymethyl pyrrolidone and caprolactam, N-hydroxyethyl pyrrolidone and caprolactam, and N-hydroxypropyl pyrrolidone and caprolactam. Non-limiting examples of carboxylic acids that can be used include: acrylic acid, methacrylic acid, itaconic acid, crotonic acid, fumaric acid, succinic acid, and maleic acid. Similarly, acrylates and (meth)acrylates include (without limitation) methyl, ethyl, butyl, octyl, ethyl hexyl acrylates and their (meth)acrylate analogues. Representative anhydrides include formic anhydride, succinic anhydride, maleic anhydride and acetic anhydride.

Non-limiting examples of lactam-containing monomers may be found in "Synthesis and polymerization of new pyrrolidone-containing methacrylate monomers" by T. P. Davis et. al. (*Polymer*, 39, 17, p 4165-4169, 1998), the publication of which is hereby incorporated herein by reference in its entirety.

Further non-limiting examples of (a) a monomer comprising at least one functionalized or unfunctionalized acryloyl moiety and at least one lactam moiety (monomer A) are presented in FIG. 3 below.

Figure 3

Monomer A Examples

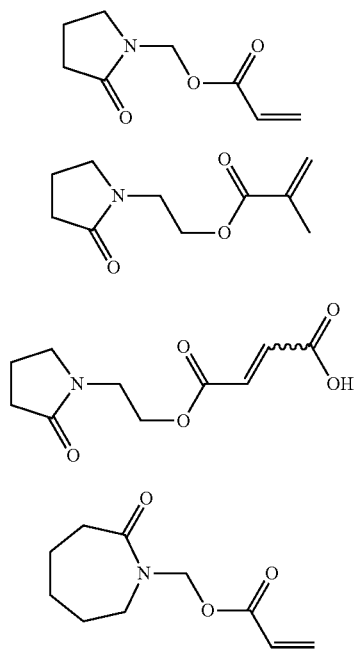

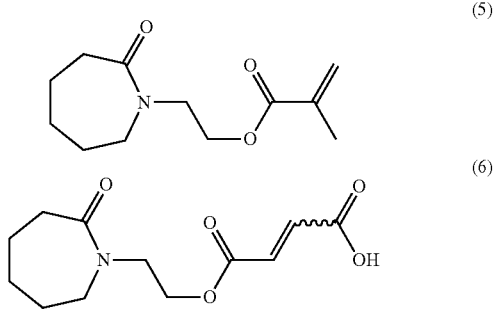

Further non-limiting examples of monomer A can be found in WO 2011/063208, the disclosure of which is hereby incorporated herein by reference in its entirety.

Non-limiting examples of cross-linkers (monomer $C_{Xn}$) include ethylidene-vinyl pyrrolidone (EVP), 1,3-divinyl imidazolidin-2-one (DVI), N,N-methylene-bisacrylamide and allyl methacrylate. Additional cross-linkers include pentaerythritol triallyl ether, methylene bisacrylamide, N,N'-divinylethylene urea, N,N'-divinylpropylene urea, divinylbenzene, ethylidene bis-3-(N-vinylpyrrolidone), 1-vinyl-3-ethylidene pyrrolidone, 3-vinyl-N-vinylpyrrolidone, 4-vinyl-N-vinylpyrrolidone, 5-vinyl-N-vinylpyrrolidone, allyl (meth)acrylate, triallylamine. Acrylic acid esters of glycol, butanediol, trimethylolpropane and glycerol as well as acrylic acid esters of glycol, butanediol, trimethylolpropane or glycerol reacted with ethylene oxide and/or epichlorohydrin, and mixtures of the previously mentioned substances are also suitable. In one non-limiting embodiment, cross-linking monomers ($C_{Xn}$) used in the so-called popcorn polymerization (proliferous polymerization) include N,N'-divinylethylene urea, ethylidene bis-3-(N-vinylpyrrolidone), 1-vinyl-3-ethylidene pyrrolidone, 3-vinyl-N-vinylpyrrolidone, 4-vinyl-N-vinylpyrrolidone, 5-vinyl-N-vinylpyrrolidone, and combinations thereof. In another non-limiting embodiment, cross-linking monomers ($C_{Xn}$) include ethylidene-vinyl pyrrolidone (EVP) and 1,3-divinyl imidazolidin-2-one (DVI).

In a second aspect, the present application provides a proliferous polymer composition comprising repeating units derived from (a) a monomer comprising at least one functionalized or unfunctionalized acryloyl moiety and at least one lactam moiety, (b) at least one monomer comprising at least one double bond, and (c) at least one cross-linker.

Non-limiting examples of a monomer comprising at least one double bond (monomer $B_{Xn}$) include N-vinyl-2-pyrrolidone ("NVP", "VP"), N-vinyl piperidone, N-vinyl caprolactam ("VCap"), derivatives thereof substituted with $C_1$ to $C_8$-alkyl groups, such as 3-methyl-, 4-methyl- or 5-methyl-N-vinylpyrrolidone, 3-methyl-N-vinylpyrrolidone, 4-methyl-N-vinylpyrrolidone, 5-methyl-N-vinylpyrrolidone, and the like. Other suitable monomers comprising at least one double bond include vinyl amides such as N-vinyl formamide and N-vinyl amine, obtainable following polymerization by hydrolysis, N-vinyl-N-methylacetamide, N-vinyl- or allyl-substituted heterocyclic compounds, such as N-vinyl pyridine, or N-allyl pyridine, N-vinyl imidazoles, which may also be substituted in the 2, 4 or 5 position with $C_1$-$C_4$-alkyl, in particular methyl or phenyl radicals, such as 1-vinyl imidazole, 1-vinyl-2-methylvinyl imidazole, and quaternized analogs thereof, such as 3-methyl-1-vinyl imidazolium chloride, 3-methyl-1-vinylimidazolium methyl sulfate, N—$C_1$- to $C_{24}$-alkyl-substituted diallyl amines or quaternized analogs thereof, such as diallyl ammonium chloride or diallyldimethylammonium chloride.

Additional examples of suitable monomers comprising at least one double bond (monomer $B_{Xn}$) are disclosed in "A novel route to substituted poly(vinyl pyrrolidone)s via simple functionalization of 1-vinyl-2-pyrrolidone in the 3-position by ring-opening reactions" by H. Reinecke et. al. (*Eur. Poly. J.,* 46 (2010) p 1557-1562). Background on the chemistry, structure, and properties of lactamic polymers can be found in "N-Vinyl Amide Polymers" by E. S. Barabas (*Encyclopedia of Polymer Science and Engineering,* 17, $2^{nd}$ ed., p 198-257, (1989)) and in "Polymers of N-Vinylpyrrolidone: Synthesis, Characterization and Uses" by F. Haaf, A. Sanner, and F. Straub (*Polymer Journal,* 17, 1, p 143-152 (1985)), the publication of each of which is hereby incorporated herein by reference in its entirety.

Additional non-limiting examples of a monomer comprising at least one double bond (monomer $B_{Xn}$) include maleic acid, maleic anhydride, isopropylmethacrylamide, acrylic acid, acrylamide, methacrylamide, 2-hydroxyethyl(meth)acrylamide, 2-hydroxyethylethylacrylamide, vinyl esters of aliphatic $C_2$-$C_{18}$-carboxylic acids, vinyl acetate (including the vinyl alcohol obtainable therefrom by hydrolysis after the polymerization), vinyl propionate, vinyl butyrate, vinyl laurate, vinyl stearate, vinyl neodecanoate VEOVA 9 and VEOVA 10, dimethylamino(m)ethyl (meth)acrylate and dimethylamino(m)ethyl(meth)acrylamide and quaternized analogs thereof, and diallyldimethylammonium chloride.

Additional insight into proliferous polymerization, or popcorn polymerization, can be found in Axmann, H.; Breitenbach, J. W., "Popcorn Polymers," *Advances in Chemistry Series* 128 (1973): 110; Breitenbach, J. W., "Proliferous polymerisation." *British Polymer Journal* 6.2 (1974): 119-131; U.S. Pat. Nos. 2,597,437; 2,340,110; 2,340,111; 6,620,900; 6,806,334; 3,277,066; 3,689,439; 3,933,766; and 4,059,552. Each of the aforementioned publications and disclosures is hereby incorporated herein by reference in its entirety.

In one non-limiting embodiment, polymers according to the present application may include more than one (a) monomer comprising at least one functionalized or unfunctionalized acryloyl moiety and/or more than one (b) monomer comprising at least one double bond (monomer B and monomer $B_{Xn}$).

Non-limiting examples of proliferous polymer compositions include those derived from the following monomeric compositions: [1] N-(2-methacryloyloxyethyl)pyrrolidone, N-vinyl-2-pyrrolidone, and 1,3-divinyl imidazolidin-2-one; [2] N-(2-methacryloyloxyethyl)pyrrolidone, N-vinyl-2-pyrrolidone, and 1-vinyl-3(E)-ethylidene pyrrolidone; [3] N-(2-methacryloyloxyethyl)pyrrolidone, N-vinyl-2-pyrrolidone, N-vinyl caprolactam and 1,3-divinyl imidazolidin-2-one; [4] N-(2-methacryloyloxyethyl)pyrrolidone, acrylic acid and 1,3-divinyl imidazolidin-2-one; [5] N-(2-acryloyloxyethyl)pyrrolidone, N-vinyl-2-pyrrolidone, and 1-vinyl-3(E)-ethylidene pyrrolidone; [6] N-(2-acryloyloxyethyl)caprolactam, N-vinyl caprolactam, and 1-vinyl-3(E)-ethylidene pyrrolidone; [7] N-(2-acryloyloxyethyl)caprolactam, 1-vinyl imidazole, and 1-vinyl-3(E)-ethylidene pyrrolidone; [8] N-(2-acryloyloxyethyl)pyrrolidone, 1-vinyl imidazole, and 1-vinyl-3(E)-ethylidene pyrrolidone; [9] N-(2-methacryloyloxyethyl)pyrrolidone, vinyl acetate and 1,3-divinyl imidazolidin-2-one; [10] N-(2-methacryloyloxyethyl)pyrrolidone, N-vinyl-2-pyrrolidone, vinyl acetate and 1,3-divinyl imidazolidin-2-one; [11] N-(2-methacryloyloxyethyl)pyrrolidone, N-vinyl-2-pyrrolidone, maleic anhydride and 1,3-divinyl imidazolidin-2-one; [12] N-(2-methacryloyloxyethyl)pyrrolidone, N-vinyl-2-pyrrolidone, dimethylamino(m)ethyl (meth)acrylamide and 1,3-divinyl imidazolidin-2-one, and the like.

In one non-limiting embodiment, the proliferous polymer composition consists essentially of (a) from about 1 to about 70% by weight of monomer A, (b) from about 20 to about 94% by weight of monomer $B_{Xn}$, and (c) from about 0.01 to about 10% by weight of monomer $C_{Xn}$.

In another non-limiting embodiment, the proliferous polymer composition consists essentially of (a) from about 1 to about 50% by weight of monomer A, (b) from about 45 to about 94% by weight of monomer $B_{Xn}$, and (c) from about 0.1 to about 5% by weight of monomer $C_{Xn}$.

The proliferous copolymer of the invention can be made by providing a polymerization mixture of (a) monomer A, optionally, (b) monomer $B_{Xa}$ and (c) monomer $C_{Xn}$, at a temperature of about 60-150° C. heating until proliferous polymerization occurs, and then recovering the desired copolymer. The final product composition is non-film forming and not soluble in solvent.

In a third aspect, the present application provides a formulation comprising a proliferous polymer composition comprising repeating units derived from (a) a monomer comprising at least one functionalized or unfunctionalized acryloyl moiety and at least one lactam moiety and (b) at least one cross-linker.

In a fourth aspect, the present application provides a formulation comprising a proliferous polymer composition comprising repeating units derived from (a) a monomer comprising at least one functionalized or unfunctionalized acryloyl moiety and at least one lactam moiety, (b) at least one monomer comprising at least one double bond, and (c) at least one cross-linker.

Non-limiting examples of formulations include malodor absorbents, adhesives, aerosols, agricultural agents, anti-soil redeposition agents, battery compositions, beverages, biocides, cementing agents, cleaning agents, coatings, conductive materials, personal care compositions, oral care compositions, hair care compositions, skin care compositions, pigments, detergents, disintegrants, dispersants, pharmaceuticals, electronic compositions, encapsulation compositions, food compositions, household industrial and institutional compositions, inks, compositions comprising iodine, compositions comprising silicate, compositions comprising peroxide, compositions comprising carbon materials, interlaminate adhesives, lithographic solutions, membranes, metal working fluids, oilfield compositions, paints, paper compositions, plasters, plastics, printing compositions, proppants, refractive index modifiers, sequestrants, self-healing coatings, shale swell inhibitors, soil release agents, static control agents, and wood-care agents.

Methods of Synthesis

In one non-limiting embodiment, the monomers $A_1$ optionally $B_{Xn}$, and $C_{Xn}$, water are held in a sealed stirred reactor under a nitrogen atmosphere and heated to about 60 to 150° C. until the reaction mixture pops, i.e. proliferous polymerization occurs, whereupon solid white particles appear. Generally, the reaction time is about 2-5 hours. The contents are then left for an additional hour, cooled and discharged. The reaction product, i.e., the cross-linked copolymer, is water-washed, filtered, and thereafter it is dried in a vacuum oven at 70° C. The yield can be about 70-98%.

Optionally, an initiator can be added to enhance the proliferous polymerization process.

The proliferous polymers according to the present application may be prepared according to the examples set out below. These examples are presented herein for purposes of illustration and are not intended to be limiting.

Example 1

General Method of Preparation of a Proliferous Polymer Composition Comprising Repeating Units Derived from N-Vinyl Pyrrolidone (VP) and Hydroxyethyl Pyrrolidone Methacrylate (HEPMA; N-(2-Methacryloyloxyethyl)Pyrrolidone) with Divinyl Imidazole (DVI) as Cross-Linker An amount of 448 g of deionized water and 10 g of HEPMA were added to a 1500 mL beaker. 3-5 drops of 50 wt % NaOH was combined with the water, HEPMA and thoroughly mixed. The pH was measured to be 9-9.5. An amount of 40 g of high purity VP (HPVP) or VP and 1 g DVI were added to the pH-adjusted water/HEPMA mixture. The reaction mixture was added to a 1-liter stainless steel Buchi reactor. The reactor was affixed to the reaction system cover plate and bolted closed to secure. The reaction agitation was commenced at a rate of 200-300 rpm. The reactor vessel was evacuated using house vacuum and sparged with ~3 bar $N_2$ allowing 5 minutes between sparging and evacuation. This process was repeated three times. Reaction mixture was heated to 100° C. After 1.5 hours, the reaction was cooled to room temperature. The reaction product was filtered using a Buchner funnel and vacuum filtering flask and washed with 1 liter of deionized water. The reaction product was reintroduced to reaction vessel with 500 mL of water and 1 g 85 wt % phosphoric acid. The reaction product was suspended in acidified water and heated to 80° C. for 1 hour then cooled, discharged and product was again filtered and rinsed with 1 liter of deionized water. The reaction product is reintroduced to the reaction vessel with 500 mL deionized water and 1.5 g 50 wt % NaOH. The reaction product suspended in caustic aqueous solution was heated for 1 hour. The reaction product was filtered and rinsed with 1 liter deionized water. A small quantity of reaction product was suspended in water and pH of the slurry was measured to be 6-7.5. The reaction product was placed in a 90° C. vacuum oven to dry for 3-5 hours.

Samples of proliferous polymer compositions in the form of powders were homogenized by grinding with a spatula to reduce the larger size particles into fine powder. Thermogravimetric analysis (TGA) was conducted in a $N_2$ gas environment with a heating profile of 10° C. per minute from ambient temperature to 600° C. The sample size was 7-10 mg.

The decomposition temperature (TGA pyrolysis) and glass transition temperature data values of sample proliferous compositions prepared according to Example 1 with varying proportions of monomers are provided in Table 1. Under these conditions, no solid proliferous polymer was observed when HEPMA was used by itself.

TABLE 1

TGA Pyrolysis and Glass Transition Temperature of Proliferous Polymers

| No. | Polymer Composition | TGA Pyrolysis (° C.) | Glass Transition (° C.) |
|---|---|---|---|
| Control A | 100% VP-DVI | 420 | 190 |
| 1B | 98% VP - 2% HEPMA - DVI | 415 | 186 |
| 1C | 95% VP - 5% HEPMA - DVI | 414 | 185 |
| 1D | 90% VP - 10% HEPMA - DVI | 412 | 185 |
| 1E | 80% VP - 20% HEPMA - DVI | 407 | 132, 183 |

Treatment of Beer

An un-stabilized all malt style beer was dosed with test polymer at indicted dose rate from a 1% hydrated slurry. The treated beer was continuously shaken and allowed a contact time of 1 hour followed by centrifugation to remove the insoluble polymer particles. The supernatant was then analyzed for Tannoid (polyphenols) and SASPL (proteins) values using the Tannometer instrument.

Tannoid Content (Tannometer)

For the analysis of Tannoids (haze active polyphenols), a solution of PVP K90 is titrated into a beer sample. The Tannoids in the beer form a precipitate with PVP K90 through hydrogen bonding. The addition of PVP K90 is plotted against the formation of haze and the maxima of the peak gives the Tannoid Content expressed as mg PVP/L beer. Lower values indicate lower Tannoid content and better predicted stability.

Saturated Ammonium Sulfate Precipitation Limit (SASPL) (Tannometer)

The analysis of haze active proteins is carried out by dosing a saturated solution of ammonium sulfate into a beer sample. The addition of ammonium sulfate into beer induces the precipitation of proteins resulting in a sudden increase in haze. The limit of precipitation is expressed as the volume of saturated ammonium sulfate solution which induces the beginning of haze formation. The Tannometer plots the haze as a function of dose rate and reports the limit of precipitation as ml of saturated ammonium sulfate solution per 100 ml beer. Higher values indicate lower protein content and better predicted stability.

TABLE 2

| Treatment | Average Particle Size (um) | Dose Rate (g/hl) | Tannoids (polyphenols) (mg PVP/L beer) | SASPL (proteins) (ml/100 ml beer) |
|---|---|---|---|---|
| Untreated Beer | — | 0 | 38.3 | 13.2 |
| PVPP (control) | 15.6 | 10 | 22.1 | 14.7 |
| PVPP-20% hydroxyethyl pyrrolidone methacrylate (HEPMA) | 26.2 | 10 | 23.4 | 14.6 |
| PVPP (control) | 15.6 | 20 | 15.7 | 16.0 |
| PVPP-20% hydroxyethyl pyrrolidone methacrylate (HEPMA) | 26.2 | 20 | 17.2 | 15.8 |

Example 2

Employing the teachings of U.S. Pat. No. 3,277,066 A (the disclosure of which is hereby incorporated herein by reference in its entirety), the following composition is prepared:

To a one-gallon autoclave can be charged 36 grams of N-(2-methacryloyloxyethyl) pyrrolidone, 360 grams of N-vinyl pyrrolidone, 3.6 grams of 50% aqueous sodium hydroxide and 52 milliliters of distilled water. The charge can be heated and maintained at 140° C. for one hour, after which it can be allowed to cool to 100° C. then maintained at that temperature. A rise of 6° C. can be noted three minutes after reaching 100° C. The mixture can be held at 100° C. for one hour, cooled to 80° C. after which 1500 milliliters of water can be added. The mixture can then be heated and maintained at 100° C. for one hour in order to extract any water soluble matter The mixture can be discharged as a white paste that filters easily. There can be provided insoluble polymer in a yield of 97% of theory.

Example 3

Employing the teachings of U.S. Pat. No. 4,451,582 A (the disclosure of which is hereby incorporated herein by reference in its entirety), the following composition is prepared based upon Example 4 therein.

6 parts of N-(2-methacryloyloxyethyl) pyrrolidone, 54 parts of N-vinylpyrrolidone, 1.2 parts of N,N'-divinylethyleneurea, 540 parts of distilled water and 6.65 ml of 0.1 N sodium hydroxide solution can be boiled in a stirred apparatus. After 15 minutes, insoluble polymer particles can be precipitated from the solution. A mixture of 540 parts of freshly distilled 1-vinyl imidazole and 10.8 parts of N,N'-divinylethyleneurea can then be added over 1.5 hours, causing very rapid growth of the polymer particles. To keep the suspension stirrable, it can be diluted with 200 parts of distilled water after 1 hour and again after 2 hours and 3 hours. After a total of 5 hours at 100° C., the polymerization is complete. The copolymer can be in the form of a moist powder. It can be taken up in 2,000 parts of water, centrifuged off, washed with 2,000 parts of water and dried in an oven under reduced pressure at 50° C. The polymer can be in the form of almost white, irregularly shaped aggregates of 0.1-3 mm diameter. The yield can be 90%.

Example 4

Employing the teachings of U.S. Pat. No. 7,611,722 B2 (the disclosure of which is hereby incorporated herein by reference in its entirety), the following pharmaceutical tablet core composition is prepared:

Tablet Core: 85.4 g of alendronate trihydrate (TEVA Assia Ltd.) and 2.6 g of xylitol (Danisco Sweeteners OY) can be granulated with 20 g water in a Diosna (model P1/6) granulator for 3 min. The granulate can be dried at 40° C. for one hour in a fluidized bed dryer and can be milled through a 0.8 mm screen. The granulate can be blended with 11 g the product of Example 1 for five minutes. One gram of magnesium stearate NF/EP (Mallinkrodt Inc.) can be added and the granulate can be further blended for an additional 0.5 minutes. The blend can be compressed using a Manesty F3 single punch tablet machine fitted with a 5 mm flat beveled punch. The tablet weight can be about 94.9 mg±1.0% RSD. The hardness of the core tablets can be 3-6 kP.

Example 5

Employing the teachings of U.S. Pat. No. Appl. 2013/0197006 A1 (the disclosure of which is hereby incorporated herein by reference in its entirety), the following soft chewable composition is prepared using the formulation presented in Table 3:

TABLE 3

| Ingredient | Milligrams |
| --- | --- |
| Praziquantel | 50 |
| Pyrantel embonate | 144 |
| Febantel microfine | 150 |
| Pork liver powder | 380 |
| Product of Example 1 | 100 |
| Croscarmellose sodium | 100 |
| Glycerin | 547.8 |
| Povidone 25 | 102.5 |
| Sodium saccharin | 4.2 |
| Sodium lauryl sulfate | 3.0 |
| Purified water | 547.8 |

Additional insight to the utility of the inventive compositions in pharmaceutical applications is disclosed in Bihler, Volker. *Polyvinylpyrrolidone excipients for pharmaceuticals: Povidone, crospovidone and copovidone.* Springer Science & Business Media, 2005 and Rowe, R. C.; Sheskey, P. J.; Quinn, M. E., *Handbook of Pharmaceutical Excipients*, Pharmaceutical Press, 2009 (the disclosure of which is hereby incorporated herein by reference in its entirety).

Example 6

Employing the teachings of U.S. Pat. No. 8,623,978 B2 (the disclosure of which is hereby incorporated herein by reference in its entirety), a composition containing an antioxidant is prepared:

In a 3 liter reaction vessel with heating jacket and drain tap at the bottom, 1600 g of distilled water, 7.0 g N-(2-methacryloylxyethyl) pyrrolidone, 144.8 g of N-vinylpyrrolidone, 3.52 g of N,N'-divinylethylene urea, 1.52 g of DL-alpha-tocopherol and 1.3 g of 5% strength sodium hydroxide solution can be introduced as initial charge and can be heated to 80° C. with stirring at a rotational speed of 100 rpm; during the heating and the polymerization, nitrogen, which can be fed into the reaction mixture at the bottom of the polymerization vessel, can be passed through the solution. The flow rate is 12 l/h. After the temperature of the reaction mixture is increased to 80° C., 0.01 g of sodium dithionite (dissolved in 5 g of water) can be added. The mixture can be kept at 80° C. and stirred continuously. The popcorn polymerization starts after ca. 30 minutes and completes after 3 hours (evident inter alia from the heat of reaction subsiding). The suspension can be filtered off and washed with water in order to remove impurities such as soluble polymer and nonpolymerized monomers. The polymer can be dried at 80° C. in a drying cabinet for 3 days. The yield of popcorn polymer can be more than 95%.

Example 7

Employing the teachings of U.S. Pat. No. 6,329,334 B1 (the disclosure of which is hereby incorporated herein by reference in its entirety), a detergent tablet composition is prepared as described below:

A pulverulent, granulated detergent comprising alkylbenzene sulfonate, 30 potassium coconut soap, nonionic surfactant (1 mol of $C_{13}$-$C_{15}$ fatty alcohol reacted with 7 moles of ethylene oxide, zeolite A, sodium carbonate, sodium metasilicate×5.5 $H_2O$, sodium citrate, sodium percarbonate, tetraacetylethylene diamine, ethylenediamine tetramethylene phosphonate, poly(acrylic acid-co-maleic acid), sodium sulfate, perfume, anti-foaming agents, enzymes, and optical brightener (combined bulk density ca 770 g/L) and the product from Example 2 can be worked in a mixer to give homogeneous blends, which can be compressed to pellets in a conventional eccentric press (sold by Korsch, type EK 0 DMS) under the conditions stated in the table, the resulting pellets weighing ca 3 g (diameter 20 mm). All of the mixtures contain 5% of the product from Example 2 to be used according to the present invention.

Example 8

Employing the teachings of U.S. Pat. No. 6,821,941 B2 (the disclosure of which is hereby incorporated herein by reference in its entirety), a disintegrant composition is prepared as described below in Table 4:

TABLE 4

| Ingredient | % Composition |
|---|---|
| Urea | 20 to 80% |
| product from Example 3 | 80 to 20% |

Example 9

Employing the teachings of U.S. Pat. No. 3,878,310 A (the disclosure of which is hereby incorporated herein by reference in its entirety), a beverage filtration agent composition such as the product of Example 1 is suitable for clarifying and rendering haze-free beverages such as juices, vinegars, beers and wines by contacting the beverages with water-insoluble, water-swellable polymeric product in the form of porous granules or beads. In addition, removal of metals via chelation by employing the teachings of U.S. Pat. No. 5,094,867 (the disclosure of which is hereby incorporated herein by reference in its entirety) is also envisioned. Also envisioned are product blends with silicates (i.e., xerogels, silicon dioxide, silica gels), carrageenan, cellulosics and other food additives as disclosed in Furia, Thomas E, in. *CRC handbook of food additives*. Vol. 1. CRC Press, 1973 (the disclosure of which is hereby incorporated herein by reference in its entirety). Additional insight to polysaccharides and their uses can be found in Whistler, R. L.; BeMiller, J. N. eds., "*Industrial Gums: Polysaccharides and Their Derivatives*," Academic Press, New York, 1993 (the disclosure of which is hereby incorporated herein by reference in its entirety). Additional insight into binding and complexation properties can be found in Doner, L. W.; Becard, G.; Irwin., P. L., "Binding of flavonoids by polyvinylpolypyrrolidone," *J. Agric. Food Chem.*, 1993, 41 (5), pp 753-757 (the disclosure of which is hereby incorporated herein by reference in its entirety). Additional insight into the science and technology of brewing beer can be found in Goldammer, Ted. *The brewers' handbook*. KVP Publishers, 1999 (the disclosure of which is hereby incorporated herein by reference in its entirety).

Example 10

Employing the teachings of U.S. Pat. No. 5,456,843 A (the disclosure of which is hereby incorporated herein by reference in its entirety) a membrane composition is prepared as described below.

A polymer solution/suspension can be prepared from 13.4% polyether sulphone (Ultrason E 3000 from BASF), 13.4% product from Example 1, 6% polyvinyl pyrrolidone in 60.3% N-methyl-2-pyrrolidone and 6.9% glycerol and spun into a hollow fibre and treated as described in U.S. Pat. No. 4,798,847. In this way a hydrophilic hollow fibre can be obtained of a pore size of 1 micrometer, whereby the particles of the active adsorbent are incorporated and immobilized in the matrix.

Example 11

Employing the teachings of U.S. Pat. No. 6,825,279 B2 (the disclosure of which is hereby incorporated herein by reference in its entirety) an inkjet receptive, printable media composition is prepared as described below.

A pre-mixture (Pre-mix #1) of 20 parts product from Example 1 and 80 parts water is prepared. Likewise, a pre-mixture (Pre-mix #2) is prepared using 20 parts Airflex 426 and 80 parts water. 70 parts of Pre-mix #1 is blended with 30 parts of Pre-mix #2. To this blend is added an additional 25 parts water and 0.7 parts ZONYL FSN. The solution can then be coated onto the substrate to be dried by heat.

Example 12

Employing the teachings of U.S. Pat. No. 7,585,554 (the disclosure of which is hereby incorporated herein by reference in its entirety) a composition suitable for use as a bioadhesive component to a wound dressing is prepared by mixing polyisobutylene (PIB) containing about 20% of the product from Example 1.

Example 13

Employing the teachings of WO2013/127737 A1 (the disclosure of which is hereby incorporated herein by reference in its entirety) a composition suitable for use as a component to a separator in an electrochemical cell is prepared as described below.

To 180 parts of a 30% aqueous dispersion of Product from Example 1 (about in size), 70 parts of a 0.5% aqueous solution of polyvinylpyrrolidone (PVP K-90) can be added and stirred for 30 minutes. While stirring, 5 parts of a 50% styrene-butadiene rubber dispersion (average particle size: 190 nm; glass transition temperature:—10° C.) are added. The dispersion is stirred for 2 hours and tested for stability after at least 24 hours. The viscosity of the dispersion obtained is about 70 cP, and has a pH of about 7.5. This composition is then coated onto a suitable PET non-woven fabric.

Example 14

Employing the teachings of U.S. Pat. No. 3,480,557 A (the disclosure of which is hereby incorporated herein by reference in its entirety) a composition suitable for the stabilization of peroxide compounds is prepared as described below.

A solid stabilized hydrogen peroxide composition from the product of Example 1 can be prepared by adding 100 grams of product from Example 1 to 300 ml. aqueous solution of hydrogen peroxide (50% $H_2O_2$) with stirring until a uniform slurry solution was obtained. The slurry solution can then be poured onto a sheet of aluminum foil (Teflon may be used if desired) to a depth of about 3 mm.

thickness. This preparation is then allowed to air dry for 6 to 7 days at which time the water and excess hydrogen peroxide evaporate leaving the product from Example 1 containing hydrogen peroxide.

Example 15

Employing the teachings of U.S. Pat. No. 3,136,755 A (the disclosure of which is hereby incorporated herein by reference in its entirety) a composition suitable for the complexation of iodine compounds is prepared as described below.

In preparing the insoluble polymeric iodine complexes, 100 parts by weight of the vacuum dried insoluble polymer from Example 2 is tumbled with 1 to 50 parts by weight of elemental iodine in any conventional ceramic or glass lined ball mill for a period of 4 to 24 hours. Usually a period of 12-14 hours is sufficient for complexing. During this time, when a sample of the iodine complex is shaken in carbon tetrachloride, there is revealed the presence of minute amounts of elemental iodine by the lavender color of the carbon tetrachloride. After complexing is accomplished, as indicated by substantially colorless carbon tetrachloride, the insoluble polymeric iodine material can be heated at 50-100° C. for 12-24 hours. It appears that this treatment converts remaining traces of elemental iodine to additional iodine-complex. This can be verified by shaking a small part of the stabilized material in carbon tetrachloride. The latter remains completely colorless. This test also substantiates the totality of the detoxification of the iodine in the complex.

Example 16

Employing the teachings of Lakouraj M. M.; Mokhtary, M., *Monatsh Chem* (2009) 140:53-56 (the disclosure of which is hereby incorporated herein by reference in its entirety) a composition suitable for the complexation of boron trifluoride compounds is prepared as described below.

To a suspension of 3 g product of Example 2 in 25 cm$^3$ CH$_2$Cl$_2$, a solution of 5 cm$^3$ BF$_3$*OEt$_2$ in 15 cm$^3$ CH$_2$Cl$_2$ can be added dropwise and the mixture is stirred for 1 h at room temperature. The resulting resin is filtered and washed with 2×10 cm$^3$ CH$_2$Cl$_2$ and dried in a vacuum desiccator to give a stable and non-hygroscopic powder.

What is claimed is:

1. A stable composition comprising a proliferous polymer composition comprising repeating units derived from:
   a) at least one monomer comprising at least one functionalized or unfunctionalized acryloyl moiety and at least one lactam moiety,
   b) at least one cross-linker and
   at least one peroxide compound.

2. A stable composition comprising a proliferous polymer composition comprising repeating units derived from:
   a) at least one monomer comprising at least one functionalized or unfunctionalized acryloyl moiety and at least one lactam moiety,
   b) at least one cross-linker and
   at least boron trifluoride compound.

3. A stable composition comprising a proliferous polymer composition comprising repeating units derived from:
   a) at least one monomer comprising at least one functionalized or unfunctionalized acryloyl moiety and at least one lactam moiety,
   b) at least one cross-linker, and
   at least one iodine compound.

4. A beverage filtration agent composition comprising a proliferous polymer composition comprising repeating units derived from:
   a) at least one monomer comprising at least one functionalized or unfunctionalized acryloyl moiety and at least one lactam moiety,
   b) at least one cross-linker, and
   at least one polysaccharide.

5. A beverage filtration agent composition comprising a polymer composition comprising repeating units derived from:
   a) at least one monomer comprising at least one functionalized or unfunctionalized acryloyl moiety and at least one lactam moiety,
   b) at least one cross-linker, and
   and at least one silicate.

6. A detergent composition comprising a proliferous polymer composition comprising repeating units derived from:
   a) at least one monomer comprising at least one functionalized or unfunctionalized acryloyl moiety and at least one lactam moiety,
   b) at least one cross-linker, and
   and at least one urea.

* * * * *